United States Patent [19]

Douglass

[11] 3,966,928
[45] June 29, 1976

[54] NOVEL DERIVATIVES OF PYRIDAZINE-2-OXIDE

[75] Inventor: Miriam L. Douglass, Piscataway, N.J.

[73] Assignee: Colgate-Palmolive Company, New York, N.Y.

[22] Filed: Feb. 21, 1974

[21] Appl. No.: 444,597

Related U.S. Application Data

[63] Continuation of Ser. No. 207,536, Dec. 13, 1971, abandoned.

[52] U.S. Cl. .................. 424/245; 424/250; 424/47; 424/59; 424/61; 424/62; 424/65; 424/71; 252/106; 252/107; 8/10.1; 260/242; 260/250 A

[51] Int. Cl.² ............ A61K 31/555; A61K 31/495; C11D 3/48

[58] Field of Search ............ 424/250, 245; 252/106, 252/107

[56] References Cited

UNITED STATES PATENTS

| | | | |
|---|---|---|---|
| 2,518,130 | 8/1960 | Limsker | 260/250 |
| 2,905,672 | 9/1959 | Steck | 260/250 A |
| 3,089,809 | 5/1963 | Kinugawa et al. | 424/250 |
| 3,185,687 | 5/1965 | Kano et al. | 260/250 A |
| 3,485,838 | 12/1969 | Irikura et al. | 260/250 A |
| 3,667,954 | 6/1972 | Itano et al. | 96/90 |

*Primary Examiner*—Donald B. Moyer
*Attorney, Agent, or Firm*—Steven J. Baron; Norman Blumenkopf; Herbert S. Sylvester

[57] ABSTRACT

Novel pyridazine-2-oxide derivatives inclusive of 3-mercaptopyridazine-2-oxides, disulfides thereof, metal salts thereof and 3-(2-oxopyridazinyl)isothiouronium compounds having particular utility as antimicrobial agents per se and in skin cleansing detergent compositions, shampoos, hair dressing and the like.

13 Claims, No Drawings

NOVEL DERIVATIVES OF PYRIDAZINE-2-OXIDE

This is a continuation of application Ser. No. 207,536, filed on December 13, 1971, now abandoned.

This invention relates to sulfur containing pyridazine-2-oxide derivatives having both antibacterial and antifungal activity, methods of manufacturing these compounds and compositions containing them.

The art is replete with antibacterial agents and varied compositions containing said agents. Heterocyclic compounds containing one or two nitrogen atoms in the ring, and substituents such as the oxide moieties attached to the cyclic nitrogen and/or carbon atoms and sulfide moieties attached to the carbon atoms have been found useful in a variety of anti-fungus and antibacterial compositions inclusive of weed killing plant or soil fungicides, nasal sprays, topical creams, topical dusting powder, shampoos, etc.

A particularly difficult medium for successful employment of an antibacterial compound is the human scalp and the hair thereon. Due to continued secretions of sebum and perspiration and deposits of dust, grease and oils on the scalp, often in part at least attributable to the use of preparations for treating the scalp and hair, particularly favorable conditions for the growth of bacteria often prevail on the scalp. Even if the hair and scalp are washed fairly frequently, bacterial growth there is generally faster than on most other parts of the human body and consequently, the actions of antibacterial compounds employed thereon are often ineffective. However, by the use of the compounds of this invention, good activity is obtained against bacteria, even when they are growing in such a favorable environment as the human hair and scalp.

The present compounds may be used in solutions, emulsions or suspensions, or as solids. They are usually in the form of aqueous solutions and may be applied to sites on which bacterial growth is to be counteracted. For ease of application to such sites, they may be included in various carrier compositions and are considered to be especially useful in hairdressing preparations and in shampoos.

In accordance with the present invention there are provided novel derivatives of pyridazine-2-oxide having the following structural formula:

I.

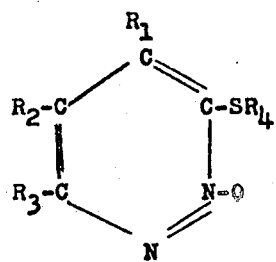

wherein $R_1$, $R_2$, $R_3$ is independently selected from the group consisting of hydrogen, straight and branched chain alkyl groups; $R_4$ is hydrogen, a metal selected from the class consisting of alkali metals, alkaline earth metal, transition metals, group IIIA, group IVA, group VA metals, a quaternary ammonium ion, $R_5R_6R_7R_8N^+$ where $R_5$, $R_6$, $R_7$, and $R_8$ may be hydrogen, alkyl or aralkyl groups, $C(NH_2)_2X$ where X may be a negative charged inorganic or organic group such as a halide, sulfates, nitrate, acetate, tartrate, citrate or saccharinate; and related disulfides of the formula:

II

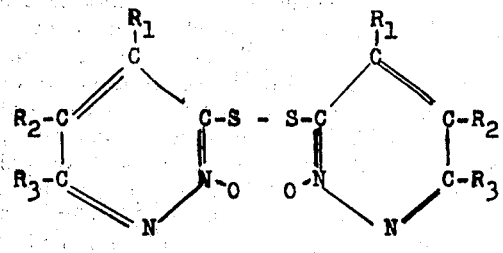

or salts of the pyridazine-2-oxides having the formula:

III

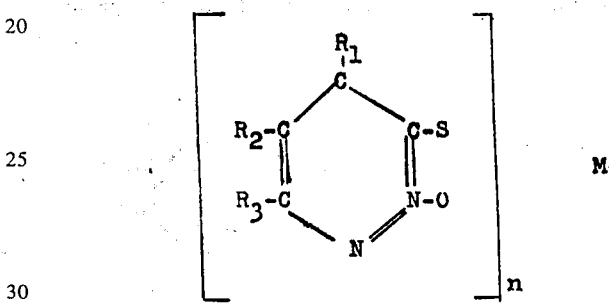

wherein $R_1$, $R_2$ and $R_3$ have the same meanings as in formula I, M is a mono-, di-, or trivalent metal selected from the class consisting of alkali metal, alkaline earth metal, transition metal, or a metal of groups IIIA, IVA, VA, and $n$ is a number from 1 to 3. Specific examples are 3-(2-oxopyridazinyl)-isothiouronium chloride, 3-mercapto-pyridazine-2-oxide, sodium or zinc salt of 3-mercaptopyridazine-2-oxide, bis [3-(2-oxopyridazinyl)] disulfide, etc.

These pyridazine-2-oxide derivatives are generally prepared by reacting 3-chloropyridazine-2-oxide with thiourea to form the thiouronium derivative which is subsequently reacted with sodium hydroxide or sodium carbonate to form the mercapto derivative thereof. Another method of preparing the mercapto derivative comprises reacting 3-chloropyridazine-2-oxide with sodium hydrosulfide. The respective salts thereof are prepared by reacting the mercapto derivative with sodium hydroxide, sodium methoxide, a zinc salt, etc. The disulfides are prepared by reacting the mercapto derivative with iodine or dilute hydrogen peroxide or other oxidizing agent.

More specifically the pyridazine-2-oxide derivatives of the instant invention are prepared from known starting materials. 3-chloropyridazine-2-oxide which may be prepared in accordance with the method described by S. Sako in Chemical Pharmaceutical Bulletin (Tokyo) Volume 11, page 261 (1963) or by any other known process is reacted with equimolecular amounts of thiourea in absolute ethanol and refluxed for one hour to give a substantially quantitative yield (97%) of 3-(2-oxopyridazinyl)isothiouronium chloride which has a melting point of 169°–171°. The mercapto derivative of pyridazine-2-oxide may be prepared by reacting one equivalent of 3-chloropyridazine-2-oxide with four equivalents of sodium hydrosulfide (10M NaSH) in an aqueous medium while stirring for one half hour at room temperature, filtering the red-orange reaction mixture, adding concentrated hydrochloric acid to a pH of 1 and collecting the light yellow product by filtration. An 83% yield of 3-mercaptopyridazine-2-oxide is obtained with the aforedefined process. Another method consists in heating a mixture of one equivalent of 3-(2-oxopyridazinyl)isothiouronium chloride prepared above, with either three equivalents of sodium hydroxide in water (5M NaOH) or four equivalents of sodium carbonate in water (0.9M $Na_2CO_3$) for one half hour, acidifying to a pH of 3 with concentrated hydrochloric acid, and collecting the light yellow reaction product by filtration. This method gives a 90% yield of 3-mercaptopyridazine-2-oxide. The sodium salt of 3-mercaptopyridazine-2-oxide is prepared in quantitative yield as a solution in water or alcohol by adding either one equivalent of sodium hydroxide to an aqueous solution or suspension of the aforedefined mercapto compound, or one equivalent of sodium methoxide in a methanol solution to a suspension of said mercapto compound, respectively. Solutions of the sodium salt of 3-mercaptopyridazine-2-oxide in any polar solvent may be prepared by adding to a solution or suspension of the mercapto compound in the desired solvent one equivalent of $Na^+ Y^-$, where $Y^-$ is a strong inorganic or organic base. Various other metal, ammonium or quaternary ammonium salts of 3-mercaptopyridazine-2-oxide may be obtained in yields of 75–90% by dissolving the mercapto pyridazine-2-oxide or the sodium salt thereof in water, adjusting the pH to 2, adding an aqueous solution of the metal salt (e.g. metal or ammonium halide, sulfate, etc.) purifying the precipitate by successively washing with water, ethyl alcohol and ethyl ether.

The reactions described above are illustrated by the following equations:

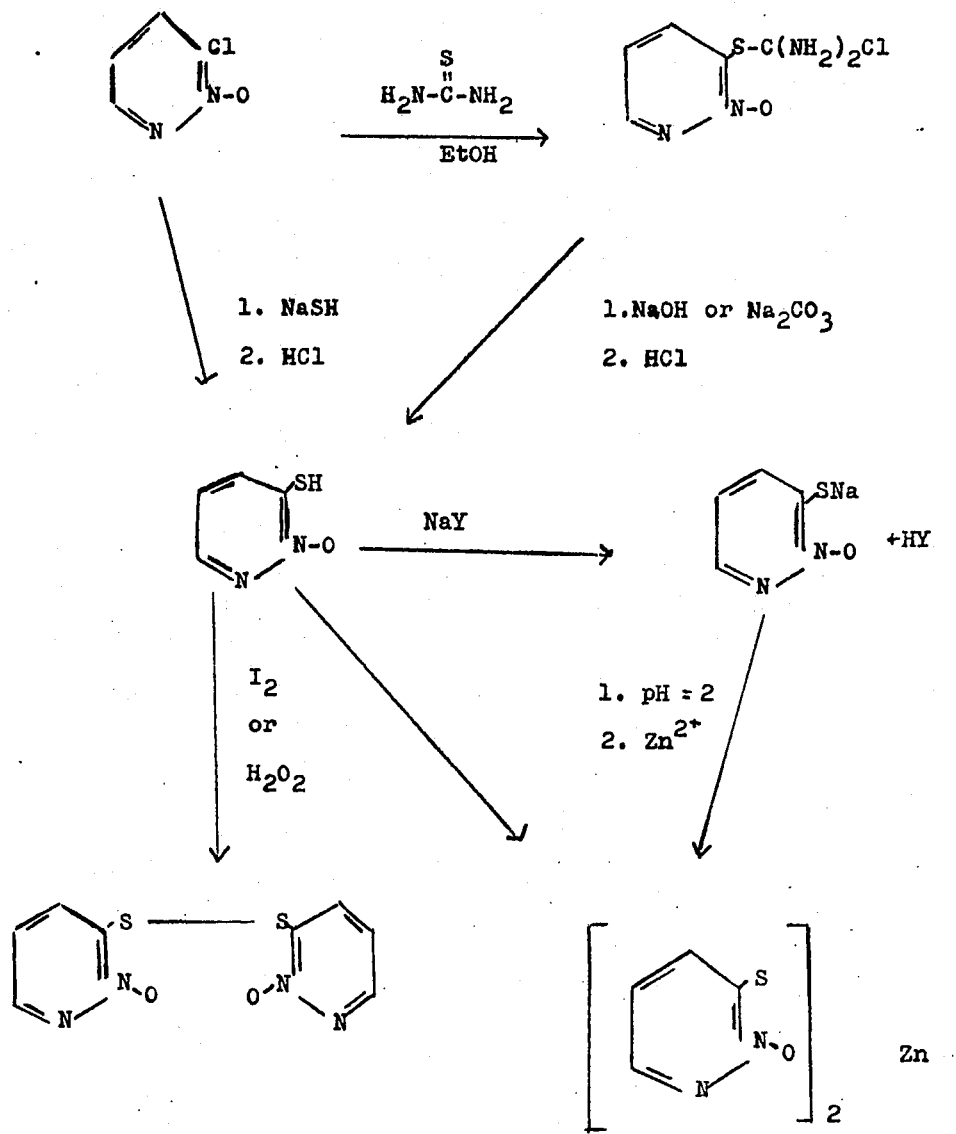

In the above equations, Y is a strong inorganic or organic base.

For clarity of presentation, the above description of methods of making the invented compounds has been given with respect to a particular starting material and corresponding derivatives thereof. However, it must be realized that such methods are also applicable to reactions utilizing different starting materials and effected by different reagents, which are equivalent in their activities to those described. Thus, instead of utilizing 3-chloropyridazine-2-oxide as the starting material, compounds having either branched or straight chain alkyl groups bonded to the pyridazine nucleus at the 4-, 5-, and/or 6-position may also be employed as the starting material. Similarly, the chloride anion in 3-(2-oxopyridazinyl)isothiouronium chloride may be replaced by another negatively charged inorganic or organic group such as fluoride, bromide, iodide, sulfate, nitrate, acetate, tartrate, citrate or saccharinate. Catalysts may be used, if desired. The solvents to be employed will be such as are conducive to dissolving the reagents and which are unaffected by the reaction.

The salt of the 3-mercaptopyridazine-2-oxide may be converted to the corresponding 3-mercaptopyridazine-2-oxide compound by treatment with any suitable chemical for removing the salt-forming cation and replacing it with hydrogen. Thus, usually an aqueous solution of an acid, preferably a dilute solution of a strong inorganic acid, such as hydrochloric acid or sulfuric acid, may be used to precipitate the 3-mercaptopyridazine-2-oxide compound. The stoichiometric quantity of acid, plus or minus 20%, will normally be employed and its dilution will usually be such that the normality is from 1 to 6 Normal. Of course, variations may be made in the types of acid and the concentrations employed, provided that sufficient acid is used to convert the salt to the acid form. Other salts of the 3-mercaptopyridazine-2-oxides may be obtained by treatment of a soluble salt thereof with a soluble metal, ammonium or quaternary ammonium or other suitable inorganic or organic salt. If the alkali metal salt is more soluble, it will often be possible to convert to other salts, such as heavy metal salts, merely by addition of a soluble heavy metal salt to the alkali metal salt of 3-mercaptopyridazine-2-oxide, preferably in aqueous solutions. However, a preferred way to produce salts other than the alkali metal salts is to acidify an aqueous solution of an alkali metal salt to a pH of about 2.5–5.0, preferably a pH of about 4, with a dilute, strong, inorganic acid, such as hydrochloric acid or sulfuric acid, although other equivalent acids may also be employed, and to add to the acidified solution a dilute aqueous solution of the appropriate metal salt, preferably the halide or sulfate thereof. Again, it is preferred to employ approximately stoichiometric proportions of such salt and the corresponding alkali metal salt of 3-mercaptopyridazine-2-oxide but variations, usually plus or minus 10 to 20% from stoichiometric proportions, are also useful. Among the salts that may be made from the alkali metal salts, e.g., the sodium, potassium and lithium salts of 3-mercaptopyridazine-2-oxide, are the zinc, calcium, magnesium, manganese, chromium, iron, copper, tungsten, nickel, barium, strontium, ammonium and quaternary ammonium, e.g., cetyltrimethyl ammonium, triethyloctadecyl ammonium and dibenzyldilauryl ammonium. The salts that may be employed include the corresponding chlorides, bromides, iodides, sulfates, phosphates, carbonates, borates, nitrates, acetates, citrates, propionates, phenates, and the other useful water soluble salts.

From 3-mercaptopyridazine-2-oxide there may be produced the corresponding bis[3-(2-oxopyridazinyl)] disulfide by oxidation. In such oxidation as shown by the equations, hydrogen atoms adjacent to the sulfur of the 3-mercaptopyridazine-2-oxide are removed, to be combined with oxygen to form water. Thus, the sulfur atoms bond together, forming the disulfide. Such oxidation may be effected by any suitable means, preferably utilizing iodine, hydrogen peroxide, or other oxidizing agent. The 3-mercaptopyridazine-2-oxide compound is usually dissolved in a suitable solvent which is capable of maintaining its liquid form during the reaction. The proportion of reactant in solvent is not considered to be critical, so long as the said reactant is substantially soluble therein.

The compounds produced, whether in the form of the 3-mercaptopyridazine-2-oxide compound, the disulfide thereof, or a salt thereof, exhibit exceptionally good antimicrobial properties. They are found to be effective in killing bacteria and in limiting the growths of various organisms. Thus, they are very effective against the organism *Pityrosporum ovale*, even when such organism is in a lipophilic environment, such as animal or mineral oil, fat or sebum. Often, when bacteria are growing in such an environment, it is difficult to have an antibacterial compound be effective against them, due to the inhibiting action of the grease or lipophilic material on the bactericide. Such inhibition may be either chemical or physical, whereby the lipophile reacts with the antibacterial compound to change it to a less effective compound or in which it prevents contact of the antibacterial product with the bacteria. In addition to the excellent utilities of the present compounds in such difficult environments, which are encountered on human or animal bodies and on the scalp or hair, it is found that these compounds are compatible with a wide variety of compositions and media in which they are employed. Thus, aqueous and alcoholic solutions of these compounds are useful, as are cosmetic preparations containing them, whether based on aqueous or lipophilic media or combinations of both such phases. For example, the present antibacterial compounds may be used in cosmetics or detergents, including liquid, solid, and semi-solid paste, cream or gelatinous preparations. They may be employed in soaps, shampoos, hairdressings, dusting powders or talcs, foot powders, "aerosol" spray preparations of various types, anti-perspirants, deodorants, antiseptics and many other materials intended for cleaning, grooming or sanitizing purposes. Perhaps, the most preferred compositions containing these compounds are those which are used in contact with the human hair or scalp, such as shampoos and hairdressings. Water or alcohol-soluble active ingredients are necessary for the formulation of transparent anti-dandruff hair products. The solubility at pH≃7 of a mixture of 3-mercaptopyridazine-2-oxide and the sodium salt thereof exceeds 0.5–1% and thus is suitable for hair dressings. 3-(2-Oxopyridazinyl)-isothiouronium chloride and the zinc salt of 3-mercaptopyridazine-2-oxide are insoluble and thus amenable to formulation only in opaque products. The preparation of a soluble thiouronium analog of the thiouronium chloride; such as the acetate, tartrate, citrate, saccharinate, or vanillate;

by double decomposition of the thiouronium chloride with the silver salt of the desired acid or by ion exchange column treatment of the thiouronium chloride, renders the active ingredient sufficiently soluble for incorporation into transparent antidandruff hair products. After use of such preparations, it appears that the effects of the present antimicrobial compounds are still obtained, apparently due to substantivity thereof on such substrates. Thus, after use of a shampoo incorporating the present materials, the hair and scalp are significantly lower in bacterial and fungus counts and even days after use, and bacterial counts are correspondingly lower. The 3-mercaptopyridazine-2-oxide, disulfides, salts and the corresponding thiouronium compounds are effective against such potent gram-positive and gram-negative organisms as *S.-aureus, Str. mitis, B. subtilis, C. acnes, E. coli, Ps. aeruginosa*, as well as against yeast and molds such as *C. albicans*, and *T. montagrophytes*.

A high level of activity against the Gram-positive bacterium *Candida acnes*, the mold *Trichophyton mentagrophytes*, and the yeast most frequently associated with dandruff, *Pityrosporum ovale*, is exhibited by the 3-thiopyridazine-2-oxides of instant invention. Such effects of these compositions have not been noted before and the active antibacterial compounds and compositions containing them have not been taught or suggested by the prior art.

In addition to the new compounds and methods for their manufacture, also within the present invention are cosmetic and detergent compositions containing such compounds as active antimicrobial ingredients, and antimicrobial uses of the compounds and such compositions. It is considered that the present bactericides are useful in a wide variety of cosmetics and antibacterial preparations, including hairdressings, hair tonics, hair waving solutions, hair dyes, bleaches, rinses, face creams, face powders, foot powders, body lotions, tanning agents, antiperspirants, sunscreens, personal deodorants, makeup preparations, bath oils, facial treatments, astringents, shaving creams, after-shave lotions and various other preparations for treatment of the hair or skin, in which antibacterial or antifungal activity is useful. Among the detergent compositions which can usefully include the present antimicrobial compounds are bar soaps, liquid soaps, soap shampoos, synthetic detergent shampoos, heavy duty synthetic organic detergents, inorganic detergent salts, pre-soak compositions, which may include enzymes, softeners, dishwashing products, synthetic detergents intended for washing hard surfaces, e.g., janitorial detergents, floor cleaning compositions and other detergent-related products such as wax-removers, organic solvent solutions of surface active materials, compositions for employment with steam cleaning machinery, car washes, and sterilizing preparations.

The cosmetic compositions may contain from 0.1 to 99% of active ingredients for the primary purpose for which they are intended, together with from 0.1 to 20%, preferably from 0.1 to 3% of a compound of the present invention. Usually, the cosmetic will contain from 1 to 100% of an aqueous or an oily phase or a solid material and sometimes, as in the cases of emulsions, will contain both aqueous and oily phases, often with a surface active material to aid in emulsification. Such surface active agents may be anionic, nonionic, cationic or amphoteric and are usually present in emulsified cosmetics in proportions of from 0.5 to 20% thereof.

Although the most preferred embodiments of the invention, hairdressings or other preparations intended for application to the hair, may be essentially lipophilic, essentially hydrophilic or emulsions, and may even be inert powders, the present compounds may be employed in any such medium. If the medium is lipophilic, there will usually be present from 50 to 99% of oil, such as mineral oil, lanolin, lanolin derivatives or other lipophilic materials, together with one or more of the present compounds. A solvent, e.g., a lower alkanol such as ethanol or isopropanol, may also be used to thin the lipophilic phase to make it easier to apply. It will usually be from 5 to 80% of the cosmetic. If the preparation is hydrophilic, it will usually contain from 50 to 99% of water, sometimes with 5 to 40% lower alkanol solvent associated therewith, plus one or more of the present anti-microbial compounds. The emulsions may have from 1 to 99%, usually from 20 to 80% of either lipophilic or hydrophilic materials, with essentially the balance thereof being of the other type. The various active ingredients utilized to give the different cosmetic preparations their desired properties are well know and are exhaustively described in the text by Edward Sagarin, Cosmetics Science and Technology (1957), and therefore, will not be listed here. However, for example, it is mentioned that with respect to hairdressings, ordinarily a mineral oil and lanolin will be employed to condition the hair and facilitate its taking of waving or combing.

Antiperspirants will normally contain an active chemical for such purpose, such as aluminum chlorhydrate. Dusting powders will normally be based on talc, silica or other special form of such materials, such as pyrogenic silica. Skin creams or lotions wll usually include stearic acid or other cold cream ingredients. The proportions of such active materials as was previously mentioned, may be varied widely, as is known in the art.

The detergent compositions in which the present antimicrobial compounds are useful may be either built or unbuilt products and may be based on anionic, cationic, nonionic and/or amphoteric surface active compounds. These are well known and are described in the text by Schwartz, Perry and Berch, Surface Active Agents and Detergents, Volume II, (1958), particularly at pages 321 and 621–625. Most frequently, the detergents employed will be anionic detergents, including the common higher fatty acid soaps of alkali metals and the synthetic anionic organic detergent salts such as those which are currently commercially used.

As examples of the anionic synthetic detergents there may be mentioned the higher alkane sulfonates, higher fatty acid monoglyceride sulfates, linear higher alkyl benzene sulfonates, higher fatty acid soaps, polyoxyethylene sulfates, hydroxyalkylene sulfonates, higher alcohol sulfates, salts of lower alcohol esters of sulfofatty acids, aromatic polyethoxy ether sulfates, acyl sarcosinates, acyl esters of isethionates and acyl N-methyl taurides, to name only a few. The salt-forming metals or other suitable salt-forming radicals for the detergents are preferably alkali metal, such as potassium or sodium but alkaline earth metals, ammonium, alkylamine, alkanolamine and magnesium salts may also be used. Some specific examples of these detergents are sodium lauryl sulfate; sodium linear tridecyl benzene sulfonate, triethanolamine lauryl sulfate; sodium or potassium coconut oil — tallow soaps; sodium lauryl sulfonate; potassium hexadecylnaphthalene sulfonate; lauryl alcohol ethylene oxide sulfate comprising four ethoxy groups per molecule; potassium stearyl glyceryl ether sulfonate; sodium lauroyl sarcosinate; and magnesium methyl tauride.

Among the nonionic surface active agents are the condensation products of alkylated phenols of ethylene oxides, alkylthioethanols with ethylene oxide, higher fatty alcohols with ethylene oxide and polyalkylene glycols or other polyols with lower alkylene oxides. Among the cationic surface active materials are N-2-aminoethyl higher alkyl amines; N-2-aminoethyl higher fatty acid amides; and quaternary ammonium compounds wherein an alkyl group is of 12 to 18 carbon atoms and other groups attached to the nitrogen are alkyls of 1 to 3 carbon atoms. Among such are ethyldimethylstearyl ammonium chloride; benzyl dimethylstearyl ammonium chloride; and trimethylcetyl ammonium bromide. The amphoteric detergents, containing both anionic and cationic groups, include the N-higher alkyl betains, and related compounds of this class. Also suitable are the fatty imidazolines and betaines containing a sulfonic group instead of the carboxylic radical.

In the built detergents, water soluble inorganic salt builders or organic builders are present to assist in dispersing, peptizing, sequestering, and alkalizing, whereby detergency is increased. Among these are the pyrophosphates, tripolyphosphates, silicates, borates, carbonates, sequisilicates and other water soluble alkaline salts, for which the salt-forming metal is usually an alkali metal, such as sodium or potassium.

Generally, in the detergent compositions, the proportion of detergent will be from 5 to 99% and preferably, there will be present from 10 to 50% thereof. The builder salts, when present, will normally be from 15 to 60% of the composition and the active antimicrobial compound will be from 0.1 to 20% thereof, preferably from 0.1 to 5% thereof and most often will be from 0.5 to 3% of the total product. The balance of such compositions will usually be an adjuvant or mixture thereof, being ordinarily from 0.1 to 25%, in total. Such adjuvants include perfumes, dyes, bleaches, softening agents, anti-redeposition agents, emollients, and brighteners. In the preferred detergents, which are essentially unbuilt shampoo preparations, there will be present from 5 to 33% of soap or synthetic organic detergent or mixture thereof, from 0.1 to 5% of antimicrobial compound and from 1 to 20% of various adjuvants, such as thickeners, foaming agents, perfumes, coloring materials, and conditioning agents. The balance will be water, with possibly from 5 to 25% of lower alkanol, if desired.

The present antimicrobial preparations, cosmetics or detergents are used in accordance with normal techniques. Thus, to sterilize or make antibacterial a particular surface, a suitable solution of the present 3-mercaptopyridazine-2-oxide or other compound of this invention may be applied to the surface and allowed to remain there or it may be removed by rinsing after a suitable time. The detergents and cosmetics are used in normal fashion. The 3-mercaptopyridazine-2-oxide, disulfides thereof, its salt or the thiouronium derivative act to kill bacteria and fungi while on the surface which is a locus thereof. Various of the present compounds are found to be especially useful against bacteria and fungi which normally are resident in the hair, such as *Micrococcus pyogenes*, var. *aureus* and *Pityrosporum ovale*.

The following examples are given to illustrate specific preferred embodiments of this invention. Clearly, the invention is not limited thereto. All temperatures are given in degrees Centigrade and all parts are by weight, unless otherwise indicated.

EXAMPLE I

Preparation of 3-(2-oxopyridazinyl)isothiouronium chloride 0.102 mole of 3-chloropyridazine-2-oxide is reacted with 0.105 mole of thiourea in 200 ml of absolute ethanol and the mixture refluxed for one hour. 3-(2-Oxopyridazinyl)isothiouronium chloride was isolated in 97% yield. This reaction product has a melting point of 169°–171°C at which temperature it decomposes.

EXAMPLE 2

Preparation of 3-mercaptopyridazine-2-oxide

One mole of the reaction product of Example I is heated with 3 moles sodium hydroxide (5M NaOH) for ½ hour. The reaction mixture is acidified to a pH = 3 by adding concentrated HCl, yielding a light yellow reaction product which is filtered. A 90% yield of the resultant product was recovered; crystallization from aqueous acetone gave pure material, mp 171.0° – 171.5°C.

EXAMPLE 3

The procedure of Example 2 was repeated except that four moles of sodium carbonate (0.9M $Na_2CO_3$) was substituted for the sodium hydroxide.

EXAMPLE 4

One mole 3-chloropyridazine-2-oxide is added to a solution of 4 moles sodium hydrosulfide in water (10M NaSH). The mixture is stirred for one half hour at room temperature. The red-orange reaction mixture is clarified by filtration. Concentrated hydrochloric acid is added to obtain a pH of 1 and the final product which is light yellow is collected by filtration. An 83% yield of 3-mercaptopyridazine-2-oxide having a melting point of 171°C is recovered.

EXAMPLE 5

Preparation of Bis[3-(2-oxopyridazinyl)] disulfide

One mole of 3 mercaptopyridazine-2-oxide is dissolved in an aqueous or alcoholic solution and is oxidized with iodine or hydrogen peroxide to produce the disulfide, which is recovered by filtration from solution, having a melting point of 232.0°–232.5°C after recrystallization from dimethylformamide.

EXAMPLE 6

Preparation of the sodium salt of 3-mercaptopyridazine-2-oxide

One mole sodium hydroxide in water is added to the reaction product of Example 2, resulting in a quantitative yield of the sodium salt in aqueous solution.

EXAMPLE 7

One mole sodium methoxide in methanol is added to the reaction product of Example 3, resulting in a quantitative yield of the sodium salt in methanol solution.

EXAMPLE 8

Preparation of the zinc salt of 3-mercaptopyridazine-2-oxide

The reaction product of Example 4 is dissolved in water and the pH adjusted to 2. To this solution is added 0.5 moles of an aqueous solution of a zinc salt such as zinc sulfate, zinc chloride, etc. The precipitate is purified by successively washing with water, ethyl alcohol and ethyl ether.

EXAMPLE 9

The reaction product of Example 5 is treated in accordance with the procedure of Example 8, yielding the zinc salt of the disulfide.

EXAMPLE 10

| Shampoo: | % |
|---|---|
| Sodium salt of 3-mercaptopyridazine-2-oxide | 1.0 |
| Potassium hexadecyl sulfate | 15.0 |
| Sodium coco-fatty acids monoglyceride sulfate | 15.0 |
| Coconut oil fatty acids diethanolamide | 5.0 |
| Lauric myristic monoethanolamide | 3.0 |
| Perfume | 1.0 |
| Lanoline esters | 1.0 |
| Sodium carboxymethyl cellulose | 0.2 |
| Free Oil | 1.5 |
| Glycerine | 2.0 |
| Water | Balance |

When used to wash human hair, the bacterial count thereon is substantially decreased, when compared with a control not containing this bactericide. Also, fungal growth is inhibited.

In lieu of the sodium salt of 3-mercaptopyridazine-2-oxide, other salts such as the zinc salt, the isothiouronium derivative or the mercapto compound per se may be utilized. Similarly beneficial results are also obtainable by utilizing other shampoo formulations, based on nonionic or cationic detergents or other of the previously mentioned synthetic detergents instead of the mentioned combination of anionic detergents. A similar result is noted when the shampoo is based on soluble higher fatty acid soap. Usually, for shampoo applications, the milder of the mentioned detergents will be selected, so as to avoid unduly drying or embrittling the hair.

EXAMPLE 11

| Hairdressings: | % |
|---|---|
| (A) | |
| Light mineral oil | 72.0 |
| Isopropyl myristate | 22.0 |
| Lanolin | 2.0 |
| Lanolin Esters | 1.5 |
| Perfume | 1.2 |
| Sodium salt of 3-mercaptopyridazine-2-oxide | 1.3 |
| (B) | |
| Light mineral oil, white deodorized | 45.0 |
| Stearic acid | 5.0 |
| Cetyl alcohol | 2.0 |
| Triethanolamine | 2.5 |
| Perfume | 0.7 |
| Zinc salt of 3-mercaptopyridazine-2-oxide | 2.0 |
| Water | 42.8 |

When human hair and the scalp are treated with the above compositions, using approximately three cubic centimeters per application, the presence of the 3-mercaptopyridazine-2-oxide salt inhibits microbial growth. By repeated daily usage over a period of weeks, diminished microbial counts are obtained. The compositions are especially useful with respect to diminishing fungal and bacterial counts and is particularly effective against *Pityrosporum ovale*, a yeast most frequently associated with dandruff, even in the presence of the sebum normally found on the hair and scalp.

In place of the particular salts of 3-mercaptopyridazine-2-oxide of the above formulas, similar proportions or variations in proportions, within the ranges described in the specification, may be employed with respect to other salts, e.g., the copper, nickel, chromium, trimethylcetyl ammonium, ammonium, alkanolamine and other such salts, the acid form and the thiouronium, with the obtaining of similar antimicrobial activities. It is noted that the bactericides are especially useful even in the normally oily environment of the scalp and hair and in the lipophilic phases of hairdressings.

Similar results are obtained when the mentioned bactericides are used in similar proportions in other cosmetics, e.g., hair setting compositions "aerosol" hair sprays, hair dyes, skin creams, talcum powders and foot powders.

The invention has been described with respect to various illustrations and embodiments thereof. However, the invention is broader than the illustrations given and it will be evident to one of ordinary skill in the art that substitutes and equivalents may be employed within the inventive concept.

What is claimed is:

1. A topical antimicrobial composition for improving the condition of the hair and skin comprising about 0.1 to 3% by weight of a compound of the formula

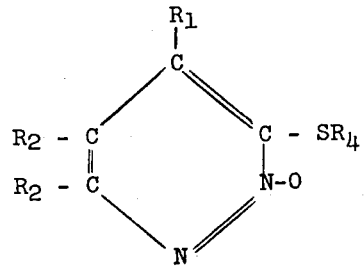

wherein $R_1$, $R_2$ and $R_3$ are each hydrogen; $R_4$ is a metal selected from alkali metals, alkaline earth metals, transistion metals, group IIIA metals, IVA metals, VA metals, and a quaternary ammonium ion of the formula $R_5R_6R_7R_8N^+$ wherein $R_5$, $R_6$, $R_7$ and $R_8$ are each independently hydrogen, and $C(NH_2)_2X$ wherein X is selected from the group consisting of halide, sulfate, nitrate, acetate, tartarate, citrate and saccharinate and a sufficient amount of a compatible, non-toxic cosmetic vehicle.

2. A composition as defined in claim 1 wherein $R_{1-3}$ is hydrogen and $R_4$ is selected from an alkali or alkaline earth metal, a transition metal and said quaternary ammonium compound wherein X is halide.

3. A composition as defined in claim 1 wherein said compound is selected from the group consisting of 3-(2-oxopyridazinyl) isothiouronium chloride, 3-mercaptopyridazine-2-oxide, Bis[3-(2-oxopyridazinyl)] disulfide, sodium salt of 3-mercaptopyridazine-2-oxide and zinc salt of 3-mercaptopyridazine-2-oxide.

4. A composition according to claim 1 which is a hair dressing.

5. A composition according to claim 1 which is a shampoo.

6. A composition according to claim 1 which is a skin cleansing detergent.

7. A topical antimicrobial composition for improving the condition of the hair and skin comprising about 0.1 to 3% by weight of a compound of the formula

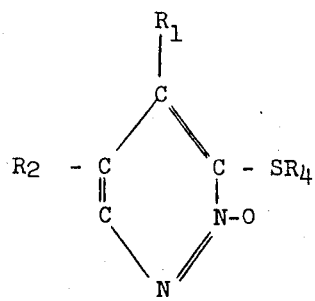

wherein $R_1$, $R_2$ and $R_3$ is hydrogen and $R_4$ is sodium and a sufficient amount of a compatible, non-toxic cosmetic vehicle.

8. A composition according to claim 7, which is a hairdressing.

9. A composition according to claim 7, which is a shampoo.

10. A composition according to claim 7, which is a skin cleansing detergent.

11. A method of improving the condition of the hair and skin by inhibiting the growth of *Pityposporum ovale* comprising applying thereto the compound as defined in claim 1.

12. A method of improving the condition of the hair and skin by inhibiting the growth of *Pitrosporum ovale* comprising applying thereto the compound as defined in claim 2.

13. A method of improving the condition the hair and skin by inhibiting the growth *Pityrosporum ovale* comprising applying thereto the compound as defined in claim 7.

* * * * *